United States Patent [19]

Braunlich et al.

[11] Patent Number: 4,999,504
[45] Date of Patent: Mar. 12, 1991

[54] REMOTE RADIATION DOSIMETRY

[75] Inventors: Peter F. Braunlich; Wolfgang Tetzlaff; Joel E. Hegland; Scott C. Jones, all of Pullman, Wash.

[73] Assignee: International Sensor Technology, Inc., Pullman, Wash.

[21] Appl. No.: 359,110

[22] Filed: May 31, 1989

Related U.S. Application Data

[63] Continuation-in-part of Ser. No. 336,015, Apr. 10, 1989, which is a continuation-in-part of Ser. No. 882,953, Jul. 7, 1986, Pat. No. 4,839,518, which is a continuation-in-part of Ser. No. 652,829, Sep. 20, 1984, Pat. No. 4,638,163, and a continuation-in-part of Ser. No. 343,000, Apr. 24, 1989, which is a continuation-in-part of Ser. No. 897,992, Aug. 19, 1986, Pat. No. 4,825,084.

[51] Int. Cl.$^5$ .................. G01T 1/115; G01T 1/11
[52] U.S. Cl. ................ 250/484.1; 250/337; 250/368; 250/458.1
[58] Field of Search .............. 250/368, 337, 354.1, 250/484.1 A, 484.1 C, 458.1

[56] References Cited

U.S. PATENT DOCUMENTS

| Re. 31,832 | 2/1985 | Samulski | 374/131 |
|---|---|---|---|
| 4,448,547 | 5/1984 | Wickersheim | 374/131 |
| 4,638,163 | 1/1987 | Braunlich et al. | 250/337 |
| 4,652,143 | 3/1987 | Wickersheim et al. | 374/161 |
| 4,752,141 | 6/1988 | Sun et al. | 374/161 |
| 4,825,084 | 4/1989 | Braunlich et al. | 250/484.1 |

Primary Examiner—Constantine Hannaher
Assistant Examiner—Edward J. Glick
Attorney, Agent, or Firm—Wells, St. John & Roberts

[57] ABSTRACT

Disclosed are methods and apparatus for remotely measuring radiation levels. Such are particularly useful for measuring relatively high levels or dosages of radiation being administered in radiation therapy. They are also useful for more general radiation level measurements where remote sensing from the remaining portions of the apparatus is desirable. The apparatus uses a beam generator, such as a laser beam, to provide a stimulating beam. The stimulating beam is preferably of wavelengths shorter than 6 microns, or more advantageously less than 2 microns. The stimulating beam is used to stimulate a remote luminescent sensor mounted in a probe which emits stored luminescent energy resulting from exposure of the sensor to ionizing radiation. The stimulating beam is communicated to the remote luminescent sensor via transmissive fiber which also preferably serves to return the emission from the luminescent sensor. The stimulating beam is advantageously split by a beam splitter to create a detector beam which is measured for power during a reading period during which the luminescent phosphor is read. The detected power is preferably used to control the beam generator to thus produce desired beam power during the reading period. The luminescent emission from the remote sensor is communicated to a suitable emission detector, preferably after filtering or other selective treatment to better isolate the luminescent emission.

39 Claims, 6 Drawing Sheets

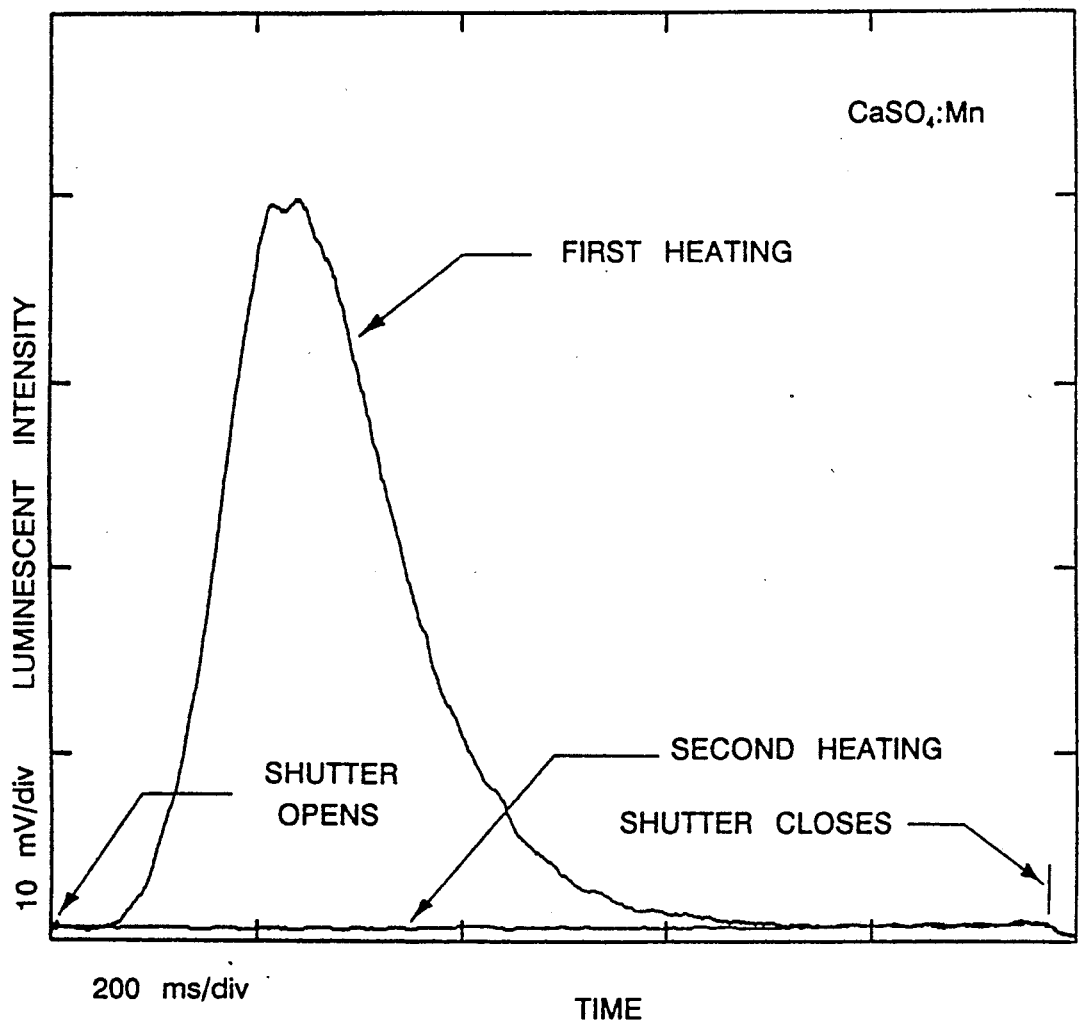

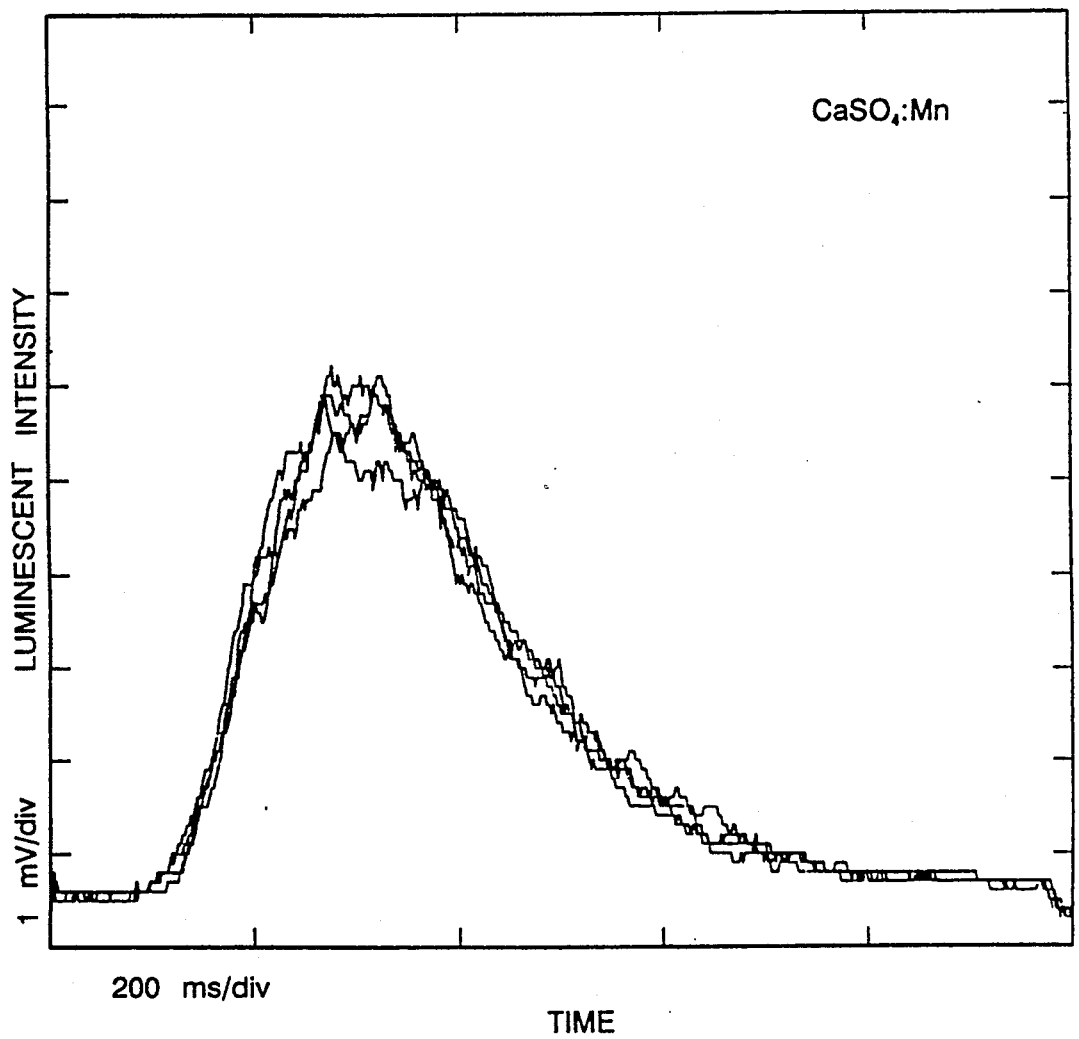

REMOTE RADIATION DOSIMETRY

This invention made with government support under Contract No. DE-AC03-85ER80226 awarded by the U.S. Department of Energy. The government has certain rights in this invention.

CROSS REFERENCE TO RELATED APPLICATIONS

This application is a continuation-in-part of U.S. patent application Ser. No. 336,015, entitled "Radiation Dosimetry by Counting Differentially Ionized Sample Areas from Heavy Charge Particle Events" filed Apr. 10, 1989; which was a continuation-in-part of allowed U.S. patent application Ser. No. 882,953, entitled "Apparatuses and Methods for Laser Reading of Thermoluminescent Phosphors", filed July 7, 1986 (now U.S. Pat. No. 4,839,518); which was a continuation-in-part of U.S. patent application Ser. No. 652,829, filed Sept. 20, 1984 (now U.S. Pat. No. 4,638,163 issued Jan. 20, 1987). This application is also a continuation-in-part of U.S. patent application Ser. No. 340,000, entitled "Radiation Dosimeters", filed Apr. 24, 1989; which was a continuation-in-part of U.S. patent application Ser. No. 897,992, entitled "Laser Readable Thermoluminescent Radiation Dosimeters and Methods for Producing Thereof", filed Aug. 19, 1986 (now U.S. Pat. No. 4,825,084 issued Apr. 25, 1989). All such applications and patents are a basis for priority under 35 USC §120 and are further hereby incorporated by reference as if set forth in full.

TECHNICAL FIELD

This invention relates to apparatus and methods for remotely measuring radiation dose information.

BACKGROUND OF THE INVENTION

There are a number of situations where radiation dose information is preferably measured remotely. For example, in the treatment of cancers and other diseases where exposure to radiation is used to kill malignant or otherwise used to treat various types of diseased tissue, it is currently impossible for the radiologists to known precisely how much radiation is being administered to the tissue being treated. The radiologist typically sets the desired radiation level on the radiation generating equipment and then treats the tissues in a localized manner for a specified period of time. The approach achieves acceptable results in many cases but has been found to vary significantly in the amount of applied radiation dose. Accordingly, there remains a strong need for in vivo radiation dosimetry equipment which can provide accurate and reliable information as to the radiation dose actually received in the tissue being treated.

There are also many industrial applications where radiation dosage or levels are preferably measured for various reasons. In and around nuclear power plants there are portions of equipment and facilities where radiation levels are sufficiently high that minimal or no exposure of personnel is allowable without protective gear. In other applications radiation levels are so high that no personnel exposure is acceptable under any condition. In many of such applications it is desirable to have measurements of radiation levels on a routine basis.

High levels of radiation are also typically derogatory to radiation measuring equipment and are often of such significance that the radiation measuring equipment cannot function accurately or reliably in the environment where radiation levels are to be measured. Accordingly, there is a continuing need for improved radiation dose measuring systems capable of remotely measuring the dosages or levels of radiation present. Such radiation measurement systems also are preferably provided with relatively small replaceable sensor assemblies which are of minimum effect on the systems being monitored.

BRIEF DESCRIPTION OF THE DRAWINGS

Preferred embodiments of the invention are illustrated in the accompanying drawings which are briefly described below.

FIG. 5 is another graph showing an example luminescent emission.

FIG. 6 is a composite graph showing 4 curves using similar radiation doses and conditions to indicate the high degree of repeatability of readings using the novel apparatuses of the invention.

DETAILED DESCRIPTION OF THE PREFERRED EMBODIMENTS

The following disclosure of the invention is submitted in furtherance of the constitutional purpose of the Patent Laws "to promote the progress of science and useful arts" (Article 1, Section 8).

Figure 1:
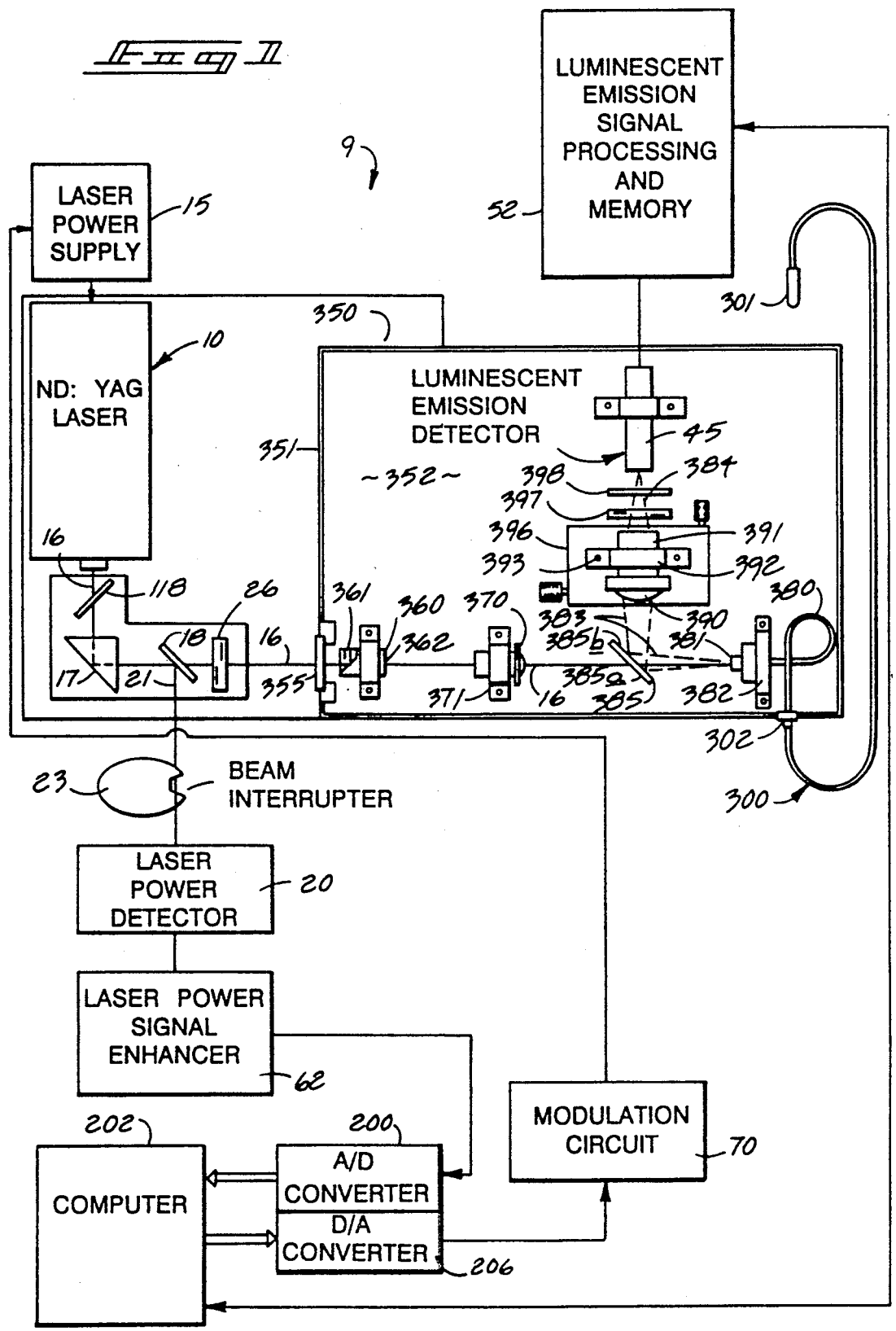
FIG. 1 is a combined diagrammatic and plan view showing the general layout of a preferred remotely sensing radiation dose measuring apparatus according to this invention.

FIG. 1 shows a preferred remotely sensing radiation dose measuring apparatus 9 made in accordance with this invention. Apparatus 9 includes a beam generator, such as laser 10, for generating and emitting a stimulating beam, such as laser beam 16. Laser 10 is powered by a laser power supply 15 which is advantageously a radio frequency power supply capable of modulation. Alternatively, silicon controlled rectifiers can be used to control the total AC power to some types of lasers thus providing the desired modulation of laser beam power. Other constructions which are otherwise controllable to obtain a desired laser beam power are also potentially useful in this invention. Lasers which utilize a DC power supply are also useful in this invention if appropriately constructed to allow modulation or control of beam power. Beam generator 10 is advantageously a neodymium yttrium aluminum garnet laser producing a laser beam 16 which is primarily coherent laser light having a stimulating beam wavelength spectrum which is narrowly centered about an approximately 1.32 micron wavelength. Another desirable laser includes a solid state diode laser (not shown). The stimulating beam generator is preferably capable of producing a beam which has a wavelength spectrum which is primarily less than 6 microns, more preferably primarily less than 2 microns. The stimulating beam wavelength spectrum is preferably different from the wavelength of the luminescent discharge which the stimulating beam causes, as explained more fully below.

The laser beam 16 from laser 10 is preferably passed through a polarizer 118 which causes the beam to be polarized thus reducing the risk of variations in the beam due to polarization changes during laser operation. The polarization changes cause variations in the reflectance and other optical properties which are undesirable. The laser 10 can preferably be provided with an internal polarization means (not shown) for polarizing the beam prior to emission from the laser device. The polarizer is of particular significance when the remote radiation dosimeter 9 is provided with a preferred stimulating beam power control system which is described below.

The stimulating beam 16 is advantageously directed in a desired orientation using an adjustable mirror assembly 17. Mirror assembly 17 is advantageously provided with a two-axis mounting which allows the reflective surface of the mirror to be adjusted about two orthogonal axes for both up and down, and left and right orientation adjustments. The mirror assembly 17 is used to direct the beam 16 to a beam controller which is advantageously provided in the form of a stimulating beam control shutter 26. Alternatively, it is possible in some cases to use beam generators which can be accurately turned on and off to achieve the desired beam control. Other means for controlling the emission or communication of the stimulating beam to the luminescent sample used as the radiation sensor and contained in probe tip 301 are also possible. The stimulating beam controller, such as shutter 26, is preferably connected to computer 202 which controls the operation of the shutter and passage of the stimulating beam therethrough.

FIG. 1 also shows a desirable laser beam power control subsystem for controlling the power of the laser beam emitted from the laser 10.

The power control subsystem includes a beam splitter 18 which is advantageously positioned to reflect a detector beam 21 consisting of only a limited portion of the laser beam 16, for example 1-10%. The power detector beam 21 is directed to a power detector, such as laser power detector 20. The laser power detector 20 can be either a continuously monitoring power detector or an intermittently monitoring power detector. A suitable power detector is a pyroelectric detector, such as a lead-zirconate-titanate detector, for example model series 350 manufactured by Barnes Engineering. Such a pyroelectric type of detector performs best when the detector beam does not impinge upon the detector in a continuous manner. Accordingly, the detector beam is preferably rendered intermittent by a suitable beam interrupter, such as rotating chopping wheel 23 shown in FIG. 1. The power detector can alternatively be a continuously monitoring detector, such as a photodiode when diode lasers are used. In apparatus including continuously monitoring power detectors there is no need for a detector beam interrupter.

The beam interrupter preferably is rotated or otherwise operated to allow measurement of the detector beam power at least once, preferably more than once, during a stimulating beam exposure period. This allows adjustment of the laser beam power during the exposure period to prevent undesirable power deviations which otherwise occur due to operational variations in the laser. More preferably a number of power measurements are made by the power modulation subsystem during the exposure periods used to stimulate the luminescent phosphor sensor 305, see FIG. 2. Such multiple beam power detection measurements allow more accurate beam power to be maintained. The beam power can be used at a relatively fixed level or varied with time as explained in the incorporated by reference U.S. Pat. No. 4,825,084.

The power level detected by detector 20 is in the form of an electronic output signal which is appropriately communicated to computer 202. This is advantageously done using a laser power signal enhancer circuitry 62 which is used to condition the signal and is described in the incorporated allowed U.S. patent application Ser. No. 882,953. Other suitable means for conditioning the detector output signal are also clearly possible. The electronic signal output from the signal enhancer 62 is communicated to a suitable analog-to-digital converter 200. The resulting digital signal is input to the computer 202 and suitably interpreted by appropriate software.

The detected power level received by the computer 202 is compared against preprogrammed operational power parameters which thus allow an appropriate laser control signal to be determined. The laser control signal either increases, decreases or continues the existing power output from the beam generator. Such signal is output to a digital-to-analog converter 206 which provides an analog signal used to control the modulation circuit 70. A preferred construction for the modulation circuit 70 is shown in the incorporated U.S. patent application Ser. No. 882,953 (now U.S. Pat. No. 4,839,518). The output from the modulation circuit is communicated to the laser power supply 15 to suitably control the power of stimulating beam 16. Other alternative means for modulating the laser power supply 15 may also be appropriate.

It should also be noted that some forms of solid state diode lasers include an integral power detection and modulation which serves to maintain the laser beam power at desired levels. Such internal power control systems of a laser may also be appropriate as power control subsystems in the current invention.

FIG. 1 also shows that the remote radiation measuring apparatus 9 includes a light-tight enclosure 350 having a surrounding case wall 351 which is used to exclude ambient light from the interior 352 of the enclosure. The stimulating beam 16 enters the enclosure 350 via a filtering window 355. Window 355 is preferably a long-wavelength passing window which filters out relatively shorter wavelength ambient light. For example, the window 355 passes approximately 80% or more of the laser beam 16 while filtering approximately 90% or more of the ambient and laser generated light having wavelengths shorter than approximately 700 nanometers. The relatively small amounts of shorter wavelength laser generated non-coherent light which infiltrate the filtering window 355 are also reduced by including a diffuse light baffle 360. The diffuse light baffle has a series of washer-shaped baffles 361 arranged to provide an aligned beam passageway 362 therethrough. The interior of the baffle is absorbing of the diffuse non-coherent light thus attenuating that component of the beam and passing the coherent laser light.

The stimulating beam 16 is also advantageously passed through a focusing lens 370. Focusing lens 370 is preferably mounted to the case 350 on an adjustable mount 371 to allow adjustment of the lens relative to the beam and other components of measuring apparatus 9. The stimulating beam passing through the focusing lens is focused onto the proximal end 381 of an intermediate optical fiber 380. The proximal end of the intermediate transmission fiber 380 is advantageously held in a 5-axis positioner 382 which allows tilting about either of two orthogonal axes which are transverse to the beam, and further allows 3-dimensional positional of the proximal end of the fiber to allow maximum transmission of the stimulating beam into the intermediate transmission fiber 380.

As shown, apparatus 9 also includes a selectively reflective mirror 385. Dichroic mirror 385 is impinged by the stimulating beam 16 on its upstream face 385a and selectively passes the relatively longer wavelength of the stimulating beam. This allows the stimulating beam to be focused onto the proximal end of the transmissive fiber 380 for communication through the transmissive fiber system to the luminescent sensor 305.

The relatively shorter wavelength visible emission from the luminescent sensor is also emitted from the proximal end 381 of the intermediate fiber 380, but in the form of a diverging beam 383 which is reflected from the downstream face 385b and toward an emission beam focusing lens 390. The emission beam focusing lens 390 is mounted in a lens tube 391 which is held by a mounting bracket 392 and fasteners 393. The mounting bracket secures the emission beam focusing lens assembly to the case, or more preferably, to an adjustable positioning device, such as an X-Y positioning table 396. The focused emission beam 384 from lens 390 is directed to the luminescent emission detector 45.

In certain forms of the apparatus built in accordance with this invention the emission beam is preferably passed through a filter which is selective to pass the relevant emission wavelength spectrum to the detector 45. Such a filter is shown as filter 398 positioned to filter the focused emission beam from focusing lens 390. A variety of suitable spectral filters are commercially available for typical emission spectra from thermoluminescent phosphors appropriately used in this invention. It may also be advantageous in certain embodiments to include an emission beam controller, such as emission beam shutter 397. Emission beam shutter 397 controls the transmission of the emission beam 384 to emission detector 45 for use in certain methods of this invention as are explained in greater detail below.

Emission detector 45 can be of a variety of types dependent upon the particular requirements of the luminescent emission being measured. Detector 45 as shown is advantageously a photomultiplier tube, well-known in the art of light detection. The detector 45 produces an electronic output signal which is communicated to appropriate equipment, such as a luminescent emission signal processing and memory unit 52. Alternatively, the general purpose or other computer 202 can receive the emission detector signal and appropriately store or route the signal for recordation in various manners, preferably in digital form for subsequent analysis. As shown, FIG. 1 indicates that the memory unit 52 is connected to the computer 202 for receiving information therefrom concerning timing and power of the stimulating beam. Other relevant data may also similarly be recorded to provide an integrated data record of the dose measuring operations. The control system can also be used to appropriate anneal the luminescent sensor and record the sampling time between annealing and stimulated emission to thereby allow measurement of the level of radiation over the relevant sampling period.

Radiation measuring apparatus 9 includes the various components described above which make up the base unit. FIG. 1 further shows that apparatus 9 includes a remote unit which is a probe assembly 300. Probe assembly 300 is for remotely sensing radiation dose or level information and allowing the sensed information to be remotely read from the luminescent sensor contained in probe assembly head 301. Probe head 301 is formed at the distal end of the detachable probe assembly 300. Probe assembly 300 is connected at its proximal end to an optically transmissive coupling 302 which allows transmission between the outer end of intermediate fiber 380 and the proximal end of probe fiber 310. The optically transmissive coupling 302 can be of various types which are commercially available. The coupling must be selected to allow transmission of both the stimulating beam spectrum and the luminescent emission spectrum between the intermediate and probe fibers.

Figure 3:
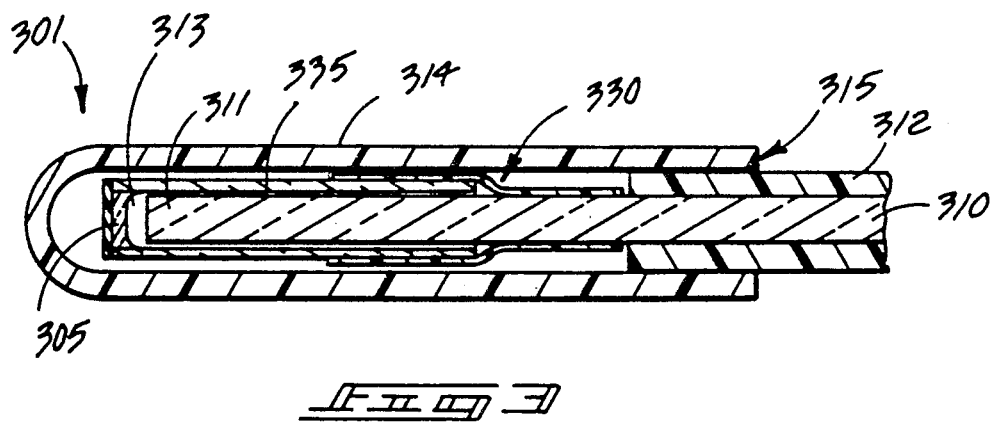
FIG. 3 is an enlarged sectional view of a preferred form of remote dosimeter sensor probe assembly used in the apparatus shown in FIG. 1. The probe assembly of FIG. 3 incorporates the sensor assembly shown in FIG. 2.

FIG. 3 shows the probe head 301 in sectional view and enlarged. The probe head is advantageously mounted upon the distal end of the probe assembly. The probe assembly includes the probe transmission fiber 310 which is preferably a single fiber between a distal end 311 and a proximal end at the probe side fitting of the transmissive coupling 302. The transmissive probe fiber can be constructed of relatively economical, widely available optical fibers when stimulating beams of wavelengths shorter than 2 microns are used. Examples of suitable fibers include fused silica fibers having a central core of approximately 600 microns diameter and having a doped silica cladding such as Superguide-G 600 available from Fiberguide Industries. When stimulating beams of wavelengths of 2-6 microns are used it is much more costly and difficult to find acceptable fibers and couplings. Sapphire fibers are capable of transmitting in this range but are very expensive. The selected optically transmissive fiber is preferably transmissive to both the stimulating beam and the luminescent emission wavelength spectrum so that a single fiber can be used. Since most thermoluminescent phosphors luminesce with visible or near visible emission spectra this requirement is typically more easily accommodated than the infrared or near infrared wavelengths of the stimulating beam.

The probe fiber is preferably provided with a an outer sheath 312 which is opaque or otherwise occlusive to ambient light which might render unreliable the transmitted luminescent emission being transmitted through the probe fiber. The probe sheath can advantageously be made of a heat-shrinkable polymer, such as heat-shrinkable Teflon tubing. The sheath is mounted coaxially over the fiber and then the fiber and sheath assembly are heated to shrink the sheath into tight contact over the exterior of the fiber. This construction provides a durable and flexible probe shaft which can be bent to radii of approximately 5 centimeters.

Figure 2:
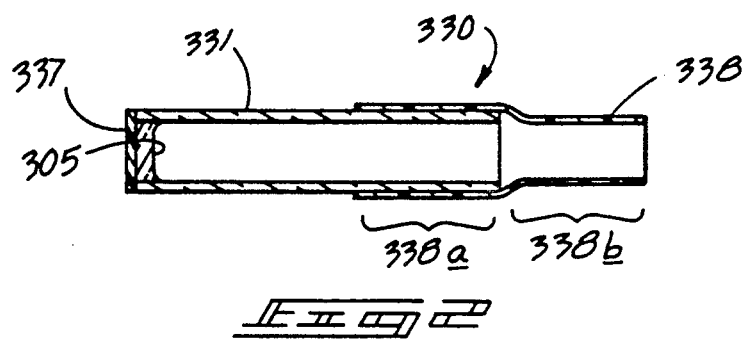
FIG. 2 is an enlarged sectional view of a preferred form of remote luminescent sensor assembly used in the apparatus shown in FIG. 1.

The probe assembly is also preferably provided with an end cap 314 which is advantageously detachable to allow installation and replacement of a sensor assembly 330, shown in isolation in FIG. 2. Alternatively, the end cap can be integral with the probe sheath. The end cap is made of a suitable protective layer, such as from a synthetic polymer, for example Teflon. The end cap is shaped with a rounded end to facilitate insertion of the probe tip into a cavity, opening or other relatively small aperture. The end cap has an opening 315 which receives the probe fiber and protective sheath therein, preferably to form a friction fit maintaining the end cap in position on the distal end of the probe assembly. This overlapping joint between the end cap and the probe-fiber sheath prevents ambient light from infiltrating at the joint therebetween. The exclusion of light can be even more appropriately accomplished using an integral probe sheath and end cap (not shown).

FIG. 2 shows a preferred detachable and replaceable luminescent sensor assembly 330 according to this invention. The sensor assembly includes a phosphor sample or sensor element support 331. The phosphor support 331 is advantageously tubular and appropriately shaped in cross-section to receive the distal end 311 of the probe fiber 310. As shown the tubular phosphor support is cylindrical and hollow to receive a cylindrical fiber end. The inside diameter of the tubular phosphor support is preferably slightly larger than the outside diameter of the transmissive fiber 310 to thereby provide a spaced annular relationship. The annular space 335 between the engaged tubular phosphor support and probe fiber provides thermal isolation between these two parts which reduces heat transfer from the phosphor support during heating of a thermoluminescent phosphor sensor element or sample 305.

The luminescent sample or sensor 305 is preferably bonded to the phosphor support within the interior of the tubular member and is thus supported about its periphery to reduce heat transfer to the support. Reduced heat transfer reduces the laser power required and the heating time. The peripheral support of the sensor is advantageously done at or near the distal end of the tubular phosphor support member 331. The phosphor support can be constructed of a variety of suitable materials such as quartz, glass, fused silica, high temperature plastics and others.

The phosphor can be a solid piece of suitable phosphor crystal or a matrix of particulate and binder which is bonded substantially according to the teachings contained in the incorporated by reference U.S. Pat. No. 4,825,084 and as described in further alternatives indicated in the incorporated by reference U.S. patent application Ser. No. 343,000. For example, the phosphor material and a heat fusible glass can be mixed with a printing vehicle and deposited within the end of a small glass tube having an interior diameter of approximately 0.8-1.0 millimeter. The phosphor material used in the luminescent sensor can be selected from a variety of suitable phosphors, particularly thermoluminescent phosphors such as $CaSO_4:Mn$ and others described in U.S. Pat. No. 4,825,084. The deposited phosphor and binder are heated to volatilize the printing vehicle and subsequently heated to soften the glass binder thus casing wetting between the binder and phosphor support. After cooling the softened glass binder fuses to both the phosphor particles an the support tube. Other alternative means for holding the luminescent phosphor sensor in location are also possible.

The sensor assembly 330 is also advantageously provided with an absorbing element or layer 337 which is preferably in direct physical contact with the luminescent sensor 305. The absorbing layer is particularly advantageously when the wavelength of the stimulating beam is not efficiently absorbed by the sensor element or other formation. The absorber layer can be selected from a variety of materials which are highly absorbing of the stimulating beam wavelength. For example, 3M brand ECP-2200 solar absorber coating can be used to increase the efficiency of absorbing 1.32 micron wavelength laser light from the YAG laser described above. Other suitable absorbing coatings can also be used. Alternatively, binders can be selected which are inherently good absorbers of the stimulating beam when the stimulating and emission spectra are sufficiently distinct.

The luminescent sensor assembly further advantageously includes a fiber connection fitting 338 which can be a suitably sized piece of heat-shrinkable Teflon tubing. The connection fitting advantageously has a phosphor support section 338a which is about the tubular phosphor support 331, and a probe shaft section 338b which is about the fiber 310 when installed as shown in FIG. 3. The inside diameter of the shaft section is preferably slightly smaller than the outside diameter of the probe shaft to provide an interference fit which is accommodated by the plastic material used to form the fit. This construction holds the sensor assembly in fixed relationship on the end of the probe shaft without the need for complex fittings, thus maintaining the size very small, approximately less than 2 millimeters outside diameter.

The invention further includes novel methods for measuring radiation at a remote location using a remotely sensing probe assembly. The methods include positioning the probe 300 with the sensor containing head 301 in a desired position for obtaining the radiation measurement. The very small size of probes possible using the present invention allows the precise monitoring of radiation within tumors during treatment or at other specific locations of interest. The properly placed luminescent sensor 305 is then exposed to the radiation being measured. For example, the radiation therapy could be administered using whatever radiation treatment which is appropriate thereby exposing the luminescent sensor to the radiation during a radiation exposure or measurement period.

After the desired radiation exposure period, the remote sensor 305 is read. The reading of sensor 305 is advantageously accomplished by controllably beaming a stimulating beam to the luminescent sensor phosphor deposit 305. The stimulating beam is emitted from the laser beam generator 10 and directed by mirror 17 to shutter 26. The shutter controls the passage of the stimulating beam therethrough. When shutter 26 is open the stimulating beam passes through the long wavelength passing window 355 and into the confined and darkened interior of the case 350. The stimulating beam is further improved by passage through the diffuse light baffle 360 which further reduces non-coherent beam components which pass through window 355. The stimulating beam 16 them is preferably focused onto the transmissive fiber system which communicates the stimulating beam to the luminescent sensor 305. The stimulating beam preferably is transmitted by at least one intermediate transmission fiber 380 thus allowing the probe 300 to more conveniently be constructed for detachment from the base portion of the device. The stimulating beam is then communicated by optically transmissive coupling 302 to the flexible probe 300 wherein the beam is transmitted along the transmissive fiber 310 from the proximal end thereof to the distal end thereof.

The stimulating beam 16 is preferably controlled during the exposure of the luminescent sensor to provide desired stimulating beam power. The stimulating beam can be controlled to provide a relatively constant beam power, or beam power can be profiled over time to help minimize incandescence or to achieve other desired operational characteristics. The power control is preferably automatically performed by the computer 202 which is preprogrammed to open shutter 26 and to begin a preprogrammed beam power schedule for the desired exposure period or periods. During the exposure period the laser power detector 20 receives at least one and preferably a number of bursts of detector beam 21. The detected power of the stimulating beam is communicated to the computer where the measured level is compared against the preprogrammed desired power level. The computer then provides a control signal to the modulation circuit 70 to control the power of the stimulating beam as desired and preprogrammed.

The stimulating beam communicated through the transmissive fiber system emits from the distal end 311 of fiber 310 and is beamed to the luminescent sensor 305, preferably across a narrow thermally isolating gap 313 of approximately 0.1-1 millimeter, more preferably approximately 0.5 millimeter. The stimulating beam thus stimulates the luminescent phosphor sensor, such as by directly heating the sensor or associated beam absorbing material 337, such as when a thermoluminescent phosphor is used. The heating or other stimulating process causes the luminescent sensor to emit a luminescent discharge which because of the close proximity is collected and transmitted into the distal end of the transmissive fiber 310. The luminescent discharge is transmitted through the transmissive fiber conduit system including fibers 310 and 380 through coupling 302.

The luminescent emission is emitted from the proximal end of the intermediate fiber 380 in a diverging beam 383 which is selectively detected to measure the amount, intensity or other characteristic of the luminescent discharge from the remote luminescent sensor. The luminescent emission beam is advantageously directed to the luminescent detector 45 using dichroic mirror 385. The emission beam 383 is also advantageously focused using lens 390 to increase the intensity of the beam directed to detector 45. Emission beam 383 is also advantageously filtered to help remove any spurious light, such as might come from the stimulating beam 16. The filtering and selection is advantageously accomplished by both the selective reflectivity of the mirror and passing the emission beam through filter 398 prior to detection by detector 45.

In a further novel process according to this invention the stimulating beam is made intermittent during the reading period of the remote sensor such as by controlling the shutter 26. The intermittent stimulating beam exposure periods are complementary with stimulating beam non-exposure periods during which the shutter 26 is closed or the stimulating beam is turned off if the beam is controlled by turning the beam generator on and off. The novel methods further involve selectively detecting the luminescent emission from the remote luminescent sensor during the non-exposure periods. The detecting of the luminescent emission is thus intermittent and performed during luminescent emission detection periods. The luminescent emission detection periods are controlled by the emission detection shutter 397 or using other suitable means for controlling impingement of the luminescent beam 383 onto the detector 45. The luminescent detection periods are preferably complementary, asynchronous and directly out of phase with the stimulating beam exposure periods. Alternatively, the luminescent emission detection periods can be asynchronous and shorter than the non-exposure periods. This method for stimulating and reading the remote sensor allows the effects of the stimulating beam to be minimized with regard to possible interference with detection of the luminescent discharge from the remote sensor. This beneficial aspect of the method is increasingly important as the wavelength spectra of the stimulating beam and luminescent emission become closer or overlapping.

The intermittent stimulating and detection can advantageously be accomplished using complementary exposure and detection periods of approximately 0.1-100 milliseconds. Total reading times for sensors stimulated with laser beams are in the range 0.5 seconds, more typically 100 milliseconds-2 seconds. The lengths of the exposure and detection periods are preferably adjusted to allow five (5) or more detection periods during the luminescent discharge period from the sensor which occurs during the reading of the sensor. More preferably, the periods are adjusted to allow a minimum of fifty (50) periods to be performed during the luminescent discharge period. The total number of emission readings taken during the reading period will typically be in the range 50-500, more preferably 50-200. The emission detection periods are typically shorter in duration than the stimulating exposure periods. For example the stimulating beam can be provided in intermittent pulses of approximately 1-10 milliseconds duration, and the detector can be provided with the luminescent emission beam during periods of 0.2-2 milliseconds. When relatively short periods are provided, the stimulating beam control and the emission detector control may no longer be adequately handled by mechanical shutters. Such embodiments may more appropriately include chopping wheels which are suitably synchronized, or alternatively, suitable electronic controls can be used, such as with a diode laser.

The emission sensed by the emission detector is preferably translated into an electronic output signal which is communicated to the luminescent emission signal processing and memory unit 52. Therein the signal is appropriately conditioned and stored, preferably in digital form, to achieve a record of the emission. The emission information directly from the emission detector or as stored in the memory unit 52, is then available for analysis to produce information which is indicative of a variable property of the luminescent discharge which is indicative of the radiation to which the remote luminescent sensor has been exposed. The maximum intensity of the luminescent emission has been found useful in determining the radiation dose to which the sensor has been exposed over time since the sensor was previously read, or read and annealed. Other information indicated by the emission signal may also be useful such as the integral of the emission intensity or other quantities derivable from the intensity. Alternatively, the emission detector may detect additional aspects of the emission other than intensity and such characteristics of the emission may be sufficiently related to the dose or level of radiation so as to allow calibration and thus determination using such alternative emission detection parameters.

The apparatus 9 and associated detected emission information is preferably calibrated by comparing the characteristic intensity or other detected parameter from the remote sensor for various exposures to known radiation levels or dosage quantities. The calibrated instrument can then be used to test unknown radiation levels or dosages.

The apparatus 9 can also be used to prepare the sensor 305 for additional dose measuring procedures. This preparation can occur automatically as a result of the reading of the sensor by stimulation with the stimulating beam to release the stored luminescent energy. Alternatively, the operation of the apparatus may require a specific annealing procedure to provide increased accuracy for the next radiation sensing and reading cycle. The annealing is easily accomplished by stimulating the luminescent sensor material 305 using the stimulating beam. The annealing can be preprogrammed for a desired beam intensity and exposure period to heat or otherwise stimulate the phosphor to release any residual luminescent energy which may remain from the prior exposure and reading cycle. The annealed sensor is then ready for additional sensing and reading operations for an indefinite lifetime dependent upon the useful service life of the luminescent phosphor, transmissive fibers and other components of the probe and remaining components making up the base portion of the remote radiation sensing apparatus.

EXAMPLE 1

A C-95 YAG-MAX laser modified for 1.32 micron photon emission was purchased from CVI Laser Corporation. This laser is water cooled and pumped by two 750 watt tungsten halogen lamps. The laser was operated in the multi-transverse mode to maximize power output at approximately 1.2 watts. The stimulating beam shutter was an electromechanical shutter from Uniblitz. The long wave pass filter was from Corion Corp. model LG-840 which eliminates most light below 0.8 micron wavelength, and transmittance of about 90% above 0.95 micron. The stimulating beam focusing lens had an effective focal length of approximately 58 millimeters. The mirror for selectively passing the stimulating beam and reflecting the luminescent emission was a Corion Corp. cold mirror model HT-700-F, which was positioned at 45° from the beam axis. This mirror has a transmittance of about 90% above 0.75 micron wavelength while reflecting about 95% below 0.68 micron wavelength. The proximal end of the intermediate fiber was provided with a modified SMA fiber optic in-line adaptor which allowed the end of the fiber to protrude slightly from the adaptor. The luminescent emission from the end of the intermediate fiber emits in a diverging cone of approximately 40°. The cone of emission light reflected off the cold mirror to a 21 millimeter effective focal length condensing lens which produces a spot of about 5 millimeters for detection by a Hamamatsu R1635 photomultiplier tube having a 10 millimeter bi-alkali photocathode and 8 dynode stages.

The transmissive fibers were Superguide-G 600 as described above. The probe shaft including the fiber and sheath had a diameter of approximately 1.8 millimeters. The phosphor support was a small pyrex tube approximately 5 millimeters long and having 0.8 millimeter inside diameter and 1.0 millimeter outside diameter. The luminescence phosphor was $CaSO_4:Mn$ which was mixed with Corning frit glass No. 7555 and Electro-Science Laboratory vehicle No. 414 in proportions of 4:2:3, respectively. The mixture was applied to the end of the glass tube and the tube was placed on a TFE sheet on end to make the layer even and to allow the applied mixture to dry. The dried tube with phosphor sensor layer was inspected and extraneous material removed from about the tube. The tube and dried layer was then heated to melt the frit glass binder. Multiple sensor assemblies were made with resulting luminescent layers ranging in thickness between 0.005 inch and 0.010 inch (127-254 microns). The sensor support assemblies were held in place by approximately 0.75 millimeter inside diameter shrink fit Teflon connectors on the probe shaft. The probe head was capped with an opaque end cap made of Teflon having a maximum diameter of 2.3 millimeters.

Figure 4A:
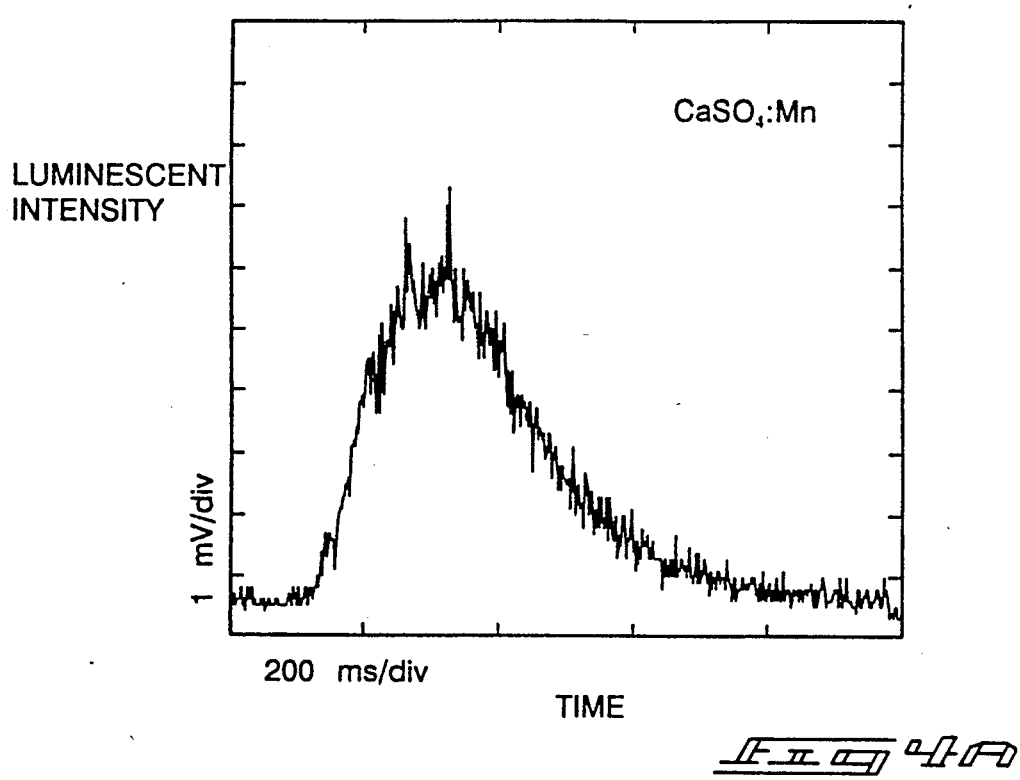
FIGS. 4A and 4B are graphs showing an example luminescent emission using an apparatus according to this invention.
Figure 4B:
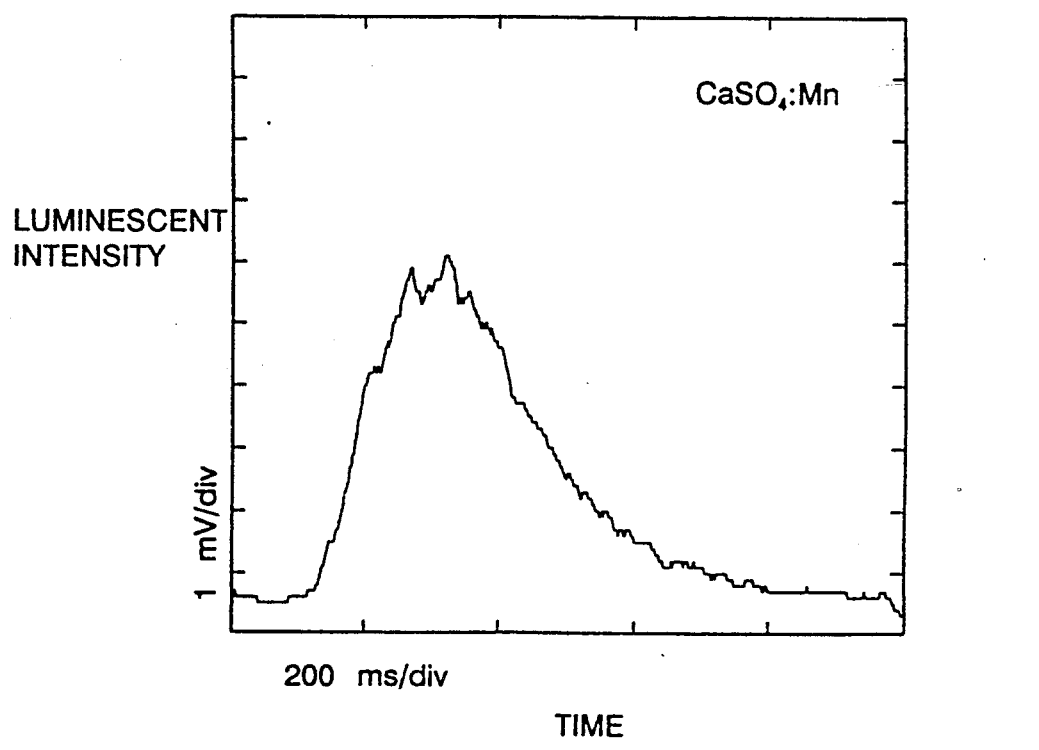

The resulting system was tested and found to provide approximately 0.35 watts at the approximately 30% of the power delivered by the laser. Sensor assemblies were exposed to 3 rad using $^{137}Cs$. FIG. 4A shows a waveform oscilloscope scan of the luminescent emission produced by heating the sensor over an exposure and reading period of approximately 1 second. The shutter opened at the start of the horizontal axis and closed about 20 milliseconds from the right margin of the growth where the signal drops. FIG. 4B shows the data of FIG. 4A after analysis using a nine point averaging to smooth the curve. Laser power output was measured at 1.16 Watt.

EXAMPLE 2

FIG. 5 shows a similar experimental run as described above in Example 1 using a 10 rad $^{137}Cs$ gamma dose. Laser output was measured at 1.35 Watt.

EXAMPLE 3

FIG. 6 shows a plurality of experimental runs as described above in Example 1 using 3 rad $^{137}Cs$ gamma exposure with laser output measured at 1.16 for 3 of the curves and 1.09 for the remaining curve. This FIG. indicates the high degree of repeatability of the results from a prototype device.

EXAMPLE 4

Figure 7:
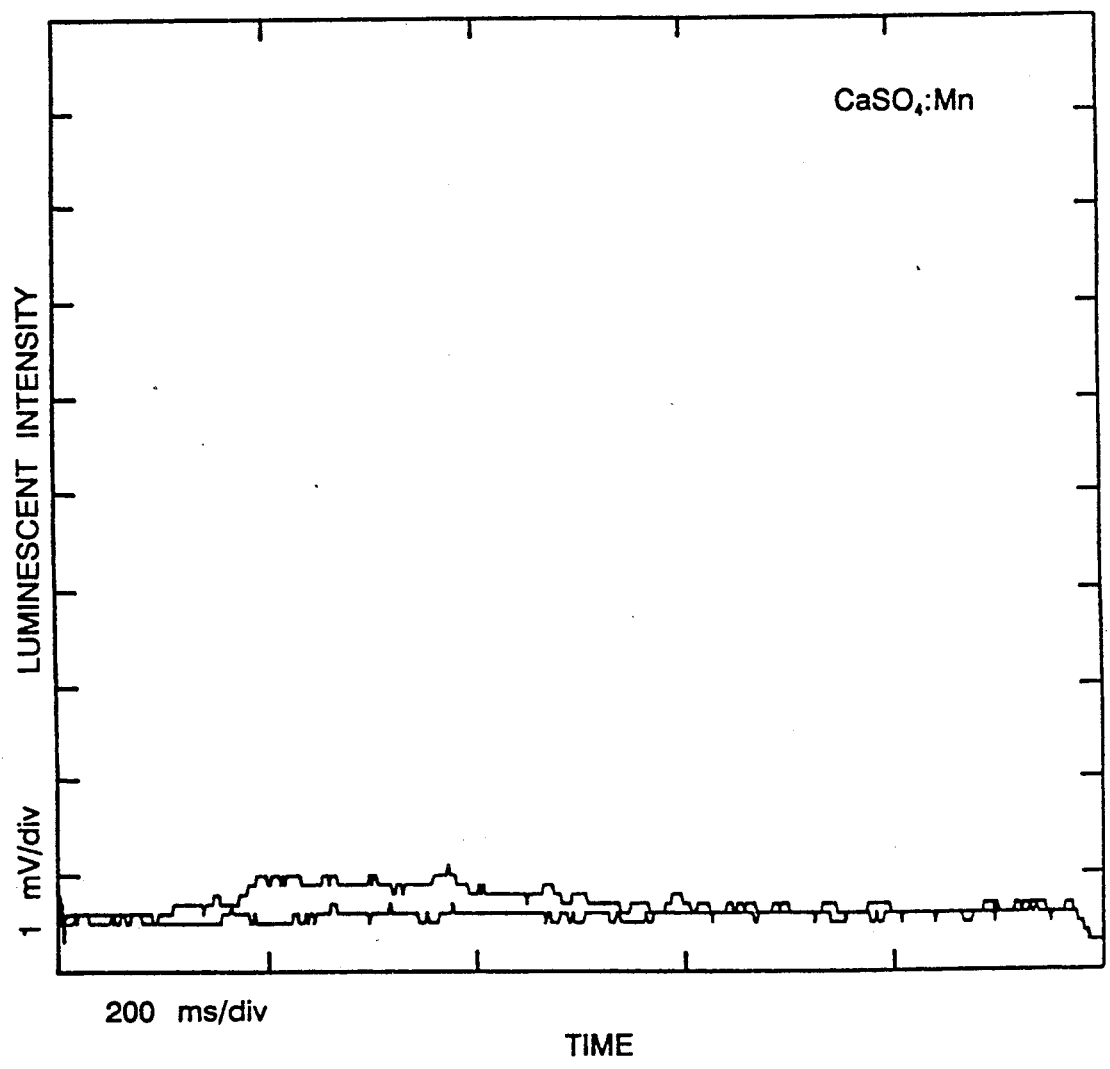
FIG. 7 is a further graph showing a relatively low radiation dose which was obtained using a device of the invention.

FIG. 7 shows a minimum response obtained using 100 millirad of $^{137}Cs$ gamma exposure and laser power of 1.14 Watt.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims approximately interpreted in accordance with the doctrine of equivalents.

We claim:

1. A remotely setting radiation dose measuring apparatus, comprising:
    at least one luminescent sensor adapted for remote mounting for exposure to radiation conditions being measured in a remote location;
    at least one beam generator for producing a stimulating beam with a stimulating beam wavelength spectrum useful for stimulating the luminescent sensor to cause a controlled luminescent discharge from said luminescent sensor with a luminescent discharge wavelength spectrum;
    beam power detection means for measuring the power of the stimulating beam at least once during an exposure period during which the stimulating beam is directed upon the luminescent sensor;

beam power control means for rapidly and adjustably modulating the power output of the stimulating beam to achieve a desired beam power;

at least one beam controller for controlling transmission of the stimulating beam to the luminescent sensor;

at least one remote transmission fiber for conveying the stimulating beam to the luminescent sensor;

at least one remote transmission fiber for conveying luminescent discharge from the luminescent sensor;

at least one luminescent discharge detector for detecting said luminescent discharge from the luminescent sensor and producing information indicative of a variable property of said luminescent discharge which is indicative of the radiation to which the remote luminescent sensor has been exposed.

2. A remotely sensing radiation dose measuring apparatus according to claim 1 wherein said at least one remote transmission fiber for conveying the stimulating beam to the luminescent sensor and said at least one remote transmission fiber for conveying luminescent discharge for the luminescent sensor, are integrated into at least one integrated transmission fiber suitable for transmitting both the stimulating beam and the luminescent discharge.

3. A remotely sensing radiation dose measuring apparatus according to claim 2 wherein said integrated transmission fiber is adapted for detachable connection with remaining portions of the dose measuring apparatus to allow removal and replacement of the integrated transmission fiber.

4. A remotely sensing radiation dose measuring apparatus according to claim 2 wherein said integrated transmission fiber is adapted for detachable connection with remaining portions of the dose measuring apparatus to allow removal and replacement of the integrated transmission fiber, and wherein said integrated transmission fiber is longitudinally partitioned into an intermediate transmission fiber and a remote probe fiber to allow a detachable probe portion containing the luminescent sensor to be removed and replaced.

5. A remotely sensing radiation dose measuring apparatus according to claim 1 wherein said integrated transmission fiber is adapted for detachable connection with remaining portions of the dose measuring apparatus to allow removal and replacement of the integrated transmission fiber.

6. A remotely sensing radiation dose measuring apparatus according to claim 1 wherein said integrated transmission fiber is adapted for detachable connection with remaining portions of the dose measuring apparatus to allow removal and replacement of the integrated transmission fiber, and wherein said integrated transmission fiber is longitudinally partitioned into an intermediate transmission fiber and a remote probe fiber to allow a detachable probe portion containing the luminescent sensor to be removed and replaced.

7. A remotely sensing radiation dose measuring apparatus according to claim 1 wherein said beam generator is a laser beam.

8. A remotely sensing radiation dose measuring apparatus according to claim 1 wherein said beam generator is a laser beam having a stimulating beam wavelength spectrum which is substantially less than 6 microns in wavelength.

9. A remotely sensing radiation dose measuring apparatus according to claim 1 wherein said beam generator is a laser beam having a stimulating beam wavelength spectrum which is substantially less than 2 microns in wavelength.

10. A remotely sensing radiation dose measuring apparatus according to claim 1 wherein the stimulating beam wavelength spectrum and the luminescent discharge wavelength spectrum are substantially distinct.

11. A remotely sensing radiation dose measuring apparatus according to claim 1 further comprising at least one light filtering means for reducing the amount of light entering an enclosure in which the luminescent discharge detector is mounted.

12. A remotely sensing radiation dose measuring apparatus according to claim 1 further comprising at least one luminescent emission selector for selectively directing luminescent emission from the at least one remote transmission fiber for conveying luminescent discharge from the luminescent sensor toward detection by the at least one luminescent discharge detector.

13. A remotely sensing radiation dose measuring apparatus, comprising:

at least one luminescent sensor adapted for remote mounting for exposure to radiation conditions being measured in a remote location;

at least one beam generator for producing a stimulating beam with a stimulating beam wavelength spectrum which is primarily shorter than 6 microns and useful for stimulating the luminescent sensor to cause a controlled luminescent discharge from said luminescent sensor with a luminescent discharge wavelength spectrum which is primarily within the visible light wavelength spectrum;

at least one beam controller for controlling transmission of the stimulating beam to the luminescent sensor;

at least one remote transmission fiber for conveying the stimulating beam to the luminescent sensor and for conveying luminescent discharge from the luminescent sensor;

at least one luminescent discharge detector for detecting said luminescent discharge from the luminescent sensor and producing information indicative of a variable property of said luminescent discharge which is indicative of the radiation to which the remote luminescent sensor has been exposed.

14. A remotely sensing radiation dose measuring apparatus according to claim 13 wherein said beam generator is a laser beam having a stimulating beam wavelength spectrum which is substantially less than 6 microns in wavelength.

15. A remotely sensing radiation dose measuring apparatus according to claim 13 wherein said beam generator is a laser beam having a stimulating beam wavelength spectrum which is substantially less than 2 microns in wavelength.

16. A remotely sensing radiation dose measuring apparatus according to claim 13 wherein said integrated transmission fiber is adapted for detachable connection with remaining portions of the dose measuring apparatus to allow removal and replacement of the integrated transmission fiber.

17. A remotely sensing radiation dose measuring apparatus according to claim 13 wherein said integrated transmission fiber is adapted for detachable connection with remaining portions of the dose measuring apparatus to allow removal and replacement of the integrated transmission fiber, and wherein said integrated transmission fiber is longitudinally partitioned into an intermediate transmission fiber and a remote probe fiber to allow a detachable probe portion containing the luminescent sensor to be removed and replaced.

18. A probe assembly for a remotely sensing radiation dose measuring apparatus, comprising:
   a phosphor support;
   a luminescent phosphor sensor mounted to the phosphor support; support with an end surface of the transmissive fiber positioned in close proximity to the luminescent phosphor sensor;
   at least one light occluding shield mounted to selectively exclude ambient light from the transmissive fiber and luminescent phosphor sensor.

19. A probe assembly according to claim 18 and further defined by said phosphor support being tubular and adapted to receive the transmissive fiber within a tubular cavity formed by the tubular phosphor support.

20. A probe assembly according to claim 18 wherein said light occluding shield includes a cladding which surrounds the transmissive fiber from a location adjacent the distal end, and an end cap which extends over and shields the phosphor support, luminescent phosphor sensor and distal end of the transmissive fiber from ambient light.

21. A probe assembly according to claim 18 wherein said probe assembly is flexible.

22. A probe assembly according to claim 18 and further comprising a stimulating beam absorber mounted to the luminescent phosphor sensor to improve absorption of a stimulating beam transmitted along said transmissive fiber to cause luminescent discharge from said luminescent phosphor sensor.

23. A luminescent sensor assembly for use in a probe assembly of a remotely sensing radiation dose measuring apparatus comprising:
   a tubular phosphor support having an interior cavity and at least one open end for allowing a transmissive fiber to be extended thereinto;
   a luminescent phosphor sensor mounted to the phosphor support.

24. A luminescent sensor assembly according to claim 23 and further comprising a mounting connector for holding the luminescent sensor assembly in a mounted position relative to a transmissive fiber when mounted therewith.

25. A luminescent sensor assembly according to claim 23 and further comprising a stimulating beam absorber mounted to the luminescent phosphor sensor to improve absorption of a stimulating beam.

26. A method for measuring radiation dose at a remote location using a remotely sensing sensor probe assembly, comprising:
   positioning the sensor probe in a desired location so that a luminescent sensor portion of said probe is positioned at a location for which radiation dose information is desired;
   exposing the luminescent sensor portion of the probe to radiation being measured;
   controllably beaming a stimulating beam through a transmissive fiber in said probe assembly to stimulate the luminescent sensor portion to emit a luminescent discharge; said beaming being with a stimulating beam having a stimulating beam wavelength spectrum;
   collecting emission from the luminescent discharge and causing transmission of the luminescent discharge along the transmissive fiber;
   selectively detecting luminescent discharge transmitted along the transmissive fiber from the remote location of the luminescent sensor portion;
   producing information indicative of a variable property of said luminescent discharge which is indicative of the radiation to which the remote luminescent sensor has been exposed.

27. A method according to claim 26 wherein said beaming is accomplished with a beam having a stimulating beam wavelength spectrum which is principally less than 6 microns in wavelength.

28. A method according to claim 26 wherein said beaming is accomplished with a beam having a stimulating beam wavelength spectrum which is principally less than 2 microns in wavelength.

29. A method according to claim 26 wherein said beaming is accomplished with a laser having a stimulating beam wavelength spectrum which is principally less than 6 microns in wavelength.

30. A method according to claim 26 wherein said beaming is accomplished with a laser having a stimulating beam wavelength spectrum which is principally less than 2 microns in wavelength.

31. A method according to claim 26 wherein said beaming is accomplished over a reading period using a plurality of intermittent stimulating beam exposure periods, and wherein said selectively detecting luminescent discharge transmitted along the transmissive fiber from the remote location of the luminescent sensor portion is accomplished over the reading period using a plurality of intermittent emission detection exposure periods which are asynchronous with respect to said intermittent stimulating beam exposure periods.

32. A method for measuring radiation dose at a remote location using a remotely sensing sensor probe assembly, comprising:
   positioning the sensor probe in a desired location so that a luminescent sensor portion of said probe is positioned at a location for which radiation dose information is desired;
   exposing the luminescent sensor portion of the probe to radiation being measured;
   emitting a stimulating beam from a beam generator which is capable of modulation to control a power level of the stimulating beam;
   controllably beaming the stimulating beam through a transmissive fiber in said probe assembly to stimulate the luminescent sensor portion during a stimulating beam exposure period to cause emission of any luminescent discharge from the luminescent sensor portion; said beaming being with a stimulating beam having a stimulating beam wavelength spectrum;
   measuring the power level of the stimulating beam at least once during a stimulating beam exposure period;
   modulating the power level of the stimulating beam to provide a desired stimulating beam power level during the stimulating beam exposure period;
   collecting emission from the luminescent discharge and causing transmission of the luminescent discharge along the transmissive fiber;
   selectively detecting luminescent discharge transmitted along the transmissive fiber from the remote location of the luminescent sensor portion;

producing information indicative of a variable property of said luminescent discharge which is indicative of the radiation to which the remote luminescent sensor has been exposed.

33. A method according to claim 32 wherein said beam is a laser beam.

34. A method according to claim 32 wherein said beaming is accomplished with a beam having a stimulating beam wavelength spectrum which is principally less than 6 microns in wavelength.

35. A method according to claim 32 wherein said beaming is accomplished with a beam having a stimulating beam wavelength spectrum which is principally less than 2 microns in wavelength.

36. A method according to claim 32 wherein said beaming is accomplished with a laser beam having a stimulating beam wavelength spectrum which is principally less than 6 microns in wavelength.

37. A method according to claim 32 wherein said beaming is accomplished with a laser beam having a stimulating beam wavelength spectrum which is principally less than 2 microns in wavelength.

38. A method according to claim 32 wherein said beaming is accomplished over a reading period using a plurality of intermittent stimulating beam exposure periods, and wherein said selectively detecting luminescent discharge transmitted along the transmissive fiber from the remote location of the luminescent sensor portion is accomplished over the reading period using a plurality of intermittent emission detection exposure periods which are asynchronous with respect to said intermittent stimulating beam exposure periods.

39. A method according to claim 32 wherein said selectively detecting is accomplished by passing the stimulating beam through a mirror which is not substantially reflective of the stimulating beam wavelength spectrum and which is effective at reflecting emission from the luminescent sensor discharge.

* * * * *